: US010376334B2

United States Patent
Fox (10) Patent No.: US 10,376,334 B2
(45) Date of Patent: Aug. 13, 2019

(54) SELF-CONTAINED LIGHTING DEVICE AND LIGHTED SUCTION DEVICE

(71) Applicant: Joshua C. Fox, Austin, TX (US)

(72) Inventor: Joshua C. Fox, Austin, TX (US)

( * ) Notice: Subject to any disclaimer, the term of this patent is extended or adjusted under 35 U.S.C. 154(b) by 0 days.

(21) Appl. No.: 15/400,195

(22) Filed: Jan. 6, 2017

(65) Prior Publication Data
US 2017/0189133 A1    Jul. 6, 2017

Related U.S. Application Data

(60) Provisional application No. 62/275,336, filed on Jan. 6, 2016.

(51) Int. Cl.
| | |
|---|---|
| *A61B 90/35* | (2016.01) |
| *F21S 9/02* | (2006.01) |
| *F21V 21/088* | (2006.01) |
| *A61B 90/30* | (2016.01) |
| *F21W 131/205* | (2006.01) |
| *F21Y 115/10* | (2016.01) |

(52) U.S. Cl.
CPC .............. *A61B 90/35* (2016.02); *A61B 90/30* (2016.02); *F21S 9/02* (2013.01); *F21V 21/088* (2013.01); *A61B 2090/309* (2016.02); *F21W 2131/205* (2013.01); *F21Y 2115/10* (2016.08)

(58) Field of Classification Search
CPC ... A61B 90/35; A61B 90/30; A61B 2090/309; F21S 9/02; F21V 15/01; F21V 21/088; F21Y 2115/10; F21W 2131/205
USPC ........................................................ 362/191
See application file for complete search history.

(56) References Cited

U.S. PATENT DOCUMENTS

| | | | |
|---|---|---|---|
| 7,306,559 B2 | 12/2007 | Williams | |
| 8,088,066 B2 | 1/2012 | Grey et al. | |
| 2006/0256575 A1* | 11/2006 | Vayser .................. | A61B 1/0623 362/573 |
| 2008/0166678 A1* | 7/2008 | Ramot .................... | A61B 1/24 433/29 |

FOREIGN PATENT DOCUMENTS

CN         103892887 A      7/2014

OTHER PUBLICATIONS

Koepke et al., "Novel Device for in situ Surgical Lighting", Biomedical Engineering Design Projects Program, The University of Texas, May 11, 2016.

* cited by examiner

*Primary Examiner* — Anh T Mai
*Assistant Examiner* — Hana S Featherly
(74) *Attorney, Agent, or Firm* — Jackson Walker LLP (57) ABSTRACT

A self-contained, sterilizable, compact light which does not include external wiring or power accessories is described herein. The lighting device is particularly useful in specialized lighting applications such as surgical applications. The lighting device preferably includes an LED and power source within a casing and can be attached in positions or on instruments within the surgical field. Alternately, the LED may be located on a suction tip while the power source and other electronics are located proximally on a handle of a suction device.

4 Claims, 7 Drawing Sheets

SELF-CONTAINED LIGHTING DEVICE AND LIGHTED SUCTION DEVICE

This application claims priority to U.S. Provisional Patent Application Ser. No. 62/275,336, entitled "Lighting Device," filed on Jan. 6, 2016, the entire contents of which are hereby incorporated by reference.

BACKGROUND

This disclosure pertains to compact, sterilizable, and easily positioned lighting devices having particular use in surgical applications.

Sterile fields are of paramount importance to surgical operating rooms as post-surgical infections can be catastrophic to those affected. Breaks in sterile technique or field are not uncommon and can lead to changes/delays in surgery or postoperative infections.

One issue that increases the risk of a break in sterile technique is wiring and tubing that passes onto and off of the surgical field. Examples include electrocautery, suction, arthroscopy lighting, suction, and similar items.

Another common issue in the operating room is visualization of the operative field in a deep hole such as a hip, pelvis or abdomen. Typical overhead lights are employed in the operating room (OR), but sometimes there is a very limited window for visualization of the desired subject, or the surgeon's head will block the light while in the path to visualize the appropriate part of the wound. In this case an additional light can be placed on the surgeon's head (such as a headlight) but these can be heavy and cumbersome, and they do not always stay in place, leading to potential breaks as the light is adjusted. This can create visualization problems for both surgeon and assistants. Another way that increased illumination and lighting can be brought to the surgical field is through lighted retractors, or instruments with fiber optic cables that bring light through a cable from off the sterile field. This, however, leads back to the initial problem of increased risk for break in sterile field by having more tubing/wiring coming from nonsterile environment.

SUMMARY

The present disclosure relates generally to an enclosed lighting source that can be easily mounted and removed in specialized applications such as surgical applications. The lighting device can be sterilized prior to use and can include a separate clip device for securing and positioning the lighting device.

The present lighting device is designed to solve problems associated with lighting in surgical and other specialized applications. It is a free standing light source that is sterilized and can be opened directly onto the operative field. It has no wiring and is disposable. In a preferred embodiment it includes a light-emitting diode (LED) in a plastic casing that is sterilized, such as by gamma radiation, and can be attached to any retractor if desired, or can be placed directly into the wound and secured with a suture. It is locatable by x-ray so it will not be left within the surgical wound. In alternative embodiments, the light source may be attached to or held in place by a disposable suction tip such as a Yankauer suction tip.

Generally speaking the lighting device includes an LED and associated electronics, such as a circuit board, power source, and heat sink, enclosed within a casing. The casing is preferably circular and plastic and may include holes or slots to facilitate attachment. In certain embodiments, a clip device accompanies the lighting device. The clip device may include a clip portion that can be attached to an item close to the area needing illumination, such as a surgical retractor, and may also include clip latches to hold the lighting device, and a front casing that will secure the lighting device within the clip.

In alternative embodiments, the LED may be placed or held at a location that is removed from the electronics and circuitry. For example, the LED could be located at the end of a suction tip while the electronics and circuitry are located in the handle of the suction device. The modified suction tip could be hollow and attach to standard OR hosing for suction, with an LED built into the distal casing for lighting and illumination with all electronics and power sources located proximally in the handle portion of the device. The proximal area is also where the switch for turning the light source on and off would preferably be located.

BRIEF DESCRIPTION OF THE DRAWINGS

FIG. 1 shows (A) a side view of an example of a lighting device and (B) a front view of an example of a lighting device.

FIG. 2 shows (A) a side view of an example of a clip device including two separate portions and (B) a side view of an example of a clip device in which an example of a lighting device has been secured and in which the portions of the clip device have been engaged and connected.

FIG. 6 shows (A) a top view of an example of a lighting device, with three LEDs visible through the surface of the casing, attached to or clipped onto a retractor with a clip attached to the bottom of the device and (B) a side view of an example lighting device and attached clip attached to or clipped onto a retractor.

DETAILED DESCRIPTION OF PREFERRED EMBODIMENTS

The present disclosure relates to a lighting device for use in specialized applications, such as surgical applications, and a clip device that can be used therewith.

Figure 1:
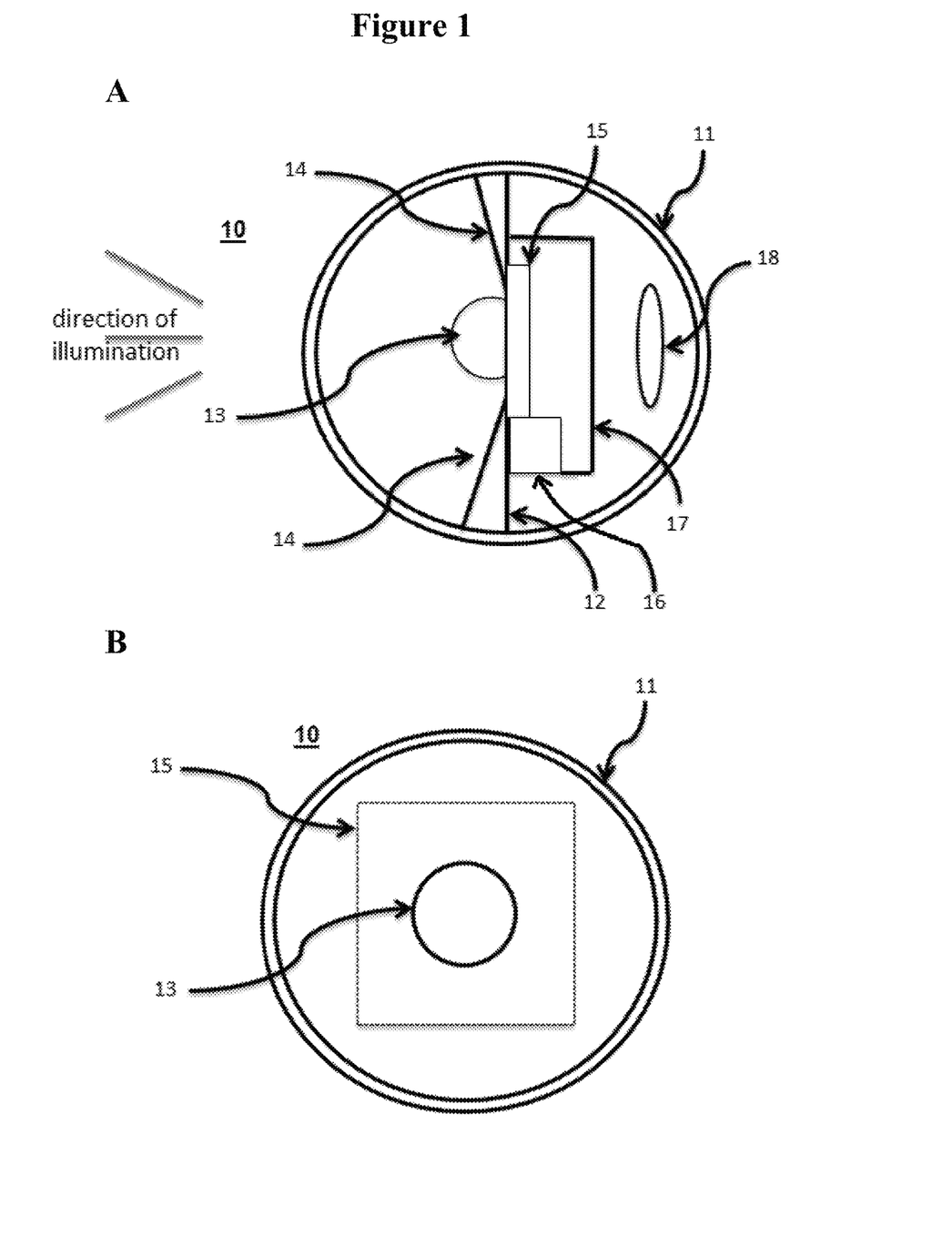

FIG. 1A shows a side view of an embodiment of the lighting device 10. Casing 11 surrounds the internal light source and electronics and is preferably plastic and sterilizable. Casing 11 should be clear or translucent to allow light to pass, or in alternative embodiments will have slots or spaces to allow light from the LED to pass. Inside casing 11 is found a central mounting surface 12 on which other components may be mounted. In particular, in this example, LED 13 is mounted on central mounting surface 12. LED 13 may be a single LED or multiple LEDs that provide the illumination or lighting. Reflectors 14 may help to direct the light from LED 13 out of the device in a forward direction, allowing for directed illumination of the field. The direction of illumination is shown in FIG. 1A. Circuit board 15 is also mounted on central mounting surface 12 in proximity to LED 13 and is used to control LED 13. Power source 16 used to provide power to LED 13 is also mounted on central mounting surface 12. Heat sink 17 is also provided as a heat sink for LED 13 and, if applicable, any additional electronics. An example of a preferred power source is a battery, although additional sources of power and heat sink options may be used. One or more mounting holes 18 are also included in casing 11 to allow for attachment to a mounting device or to allow passage of a suture for direct mounting in or on a surgical field. Preferably these mounting holes pass through the body of the lighting device 10 but are surrounded by casing 11 so that the interior of casing 11 remains protected. FIG. 1B shows a front view of an embodiment of lighting device 10. Again, casing 11 surrounds LED 13 and circuit board 15.

Figure 2:
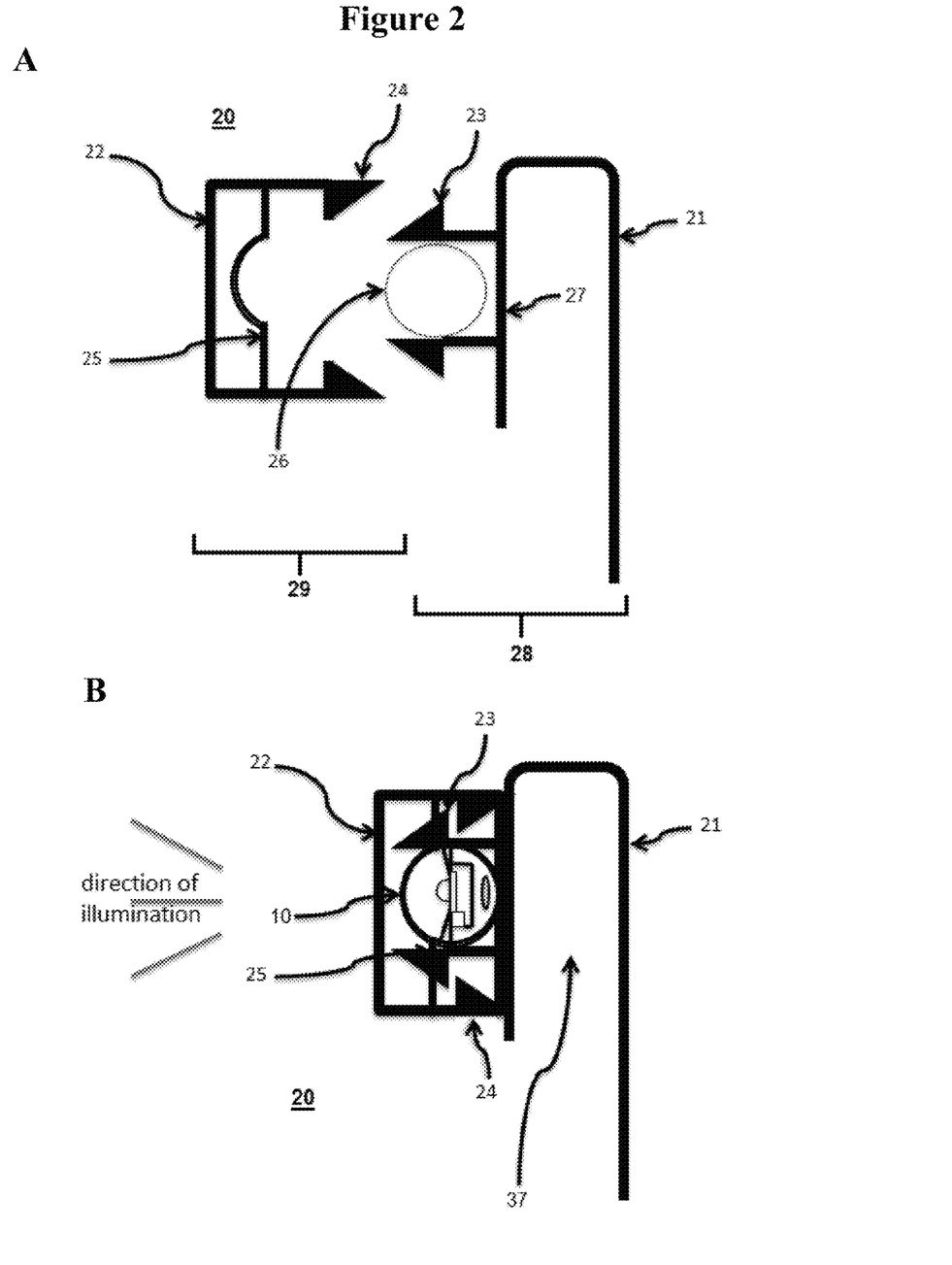

Some embodiments of the lighting device also include a clip device 20, as shown in a side view in FIG. 2A. Clip device 20 is made up of two separate portions—clip portion 28 and attachment portion 29. Clip portion 28 includes clip 21 which allows for mounting of lighting device 10 to a variety of places, including most standard retractors used in an operating room (OR). On a portion of clip 21 is located one or more clip latches 23 that will allow lighting device 10 to be anchored within and secured to clip device 20. In the embodiment seen in FIG. 2A, clip 21 is bent, with clip latches 23 secured to a front clip portion 27. Within attachment portion 29 is front casing 22 and inner contour 25. Inner contour 25 is shaped to fit around lighting device 10 when it is placed within clip device 20 to hold it in a steady position. Lighting space 26 illustrates the preferred placement of lighting device 10. Front casing 22 provides additional protection for lighting device 10. Both inner contour 25 and front casing 22 should be clear or translucent to allow light to pass and are preferably made of plastic. Attachment portion 29 also includes one or more attachment latches 24 which engage clip latches 23 on clip portion 28 in order to secure attachment portion 29 to clip portion 28, preferably with lighting device 10 located at lighting space 26. This is also shown in FIG. 2B, in which attachment latches 24 have moved past clip latches 23 and lighting device 10 is held in place by inner contour 25. Front casing 22 is in the general direction of illumination provided by lighting device 10 and protects lighting device 10 while in use. Clip 21 allows mounting of clip device 20 and lighting device 10, with clip space 37 providing an area where clip device 20 could be attached or clamped to a standard operative retractor, for example.

Figure 3:
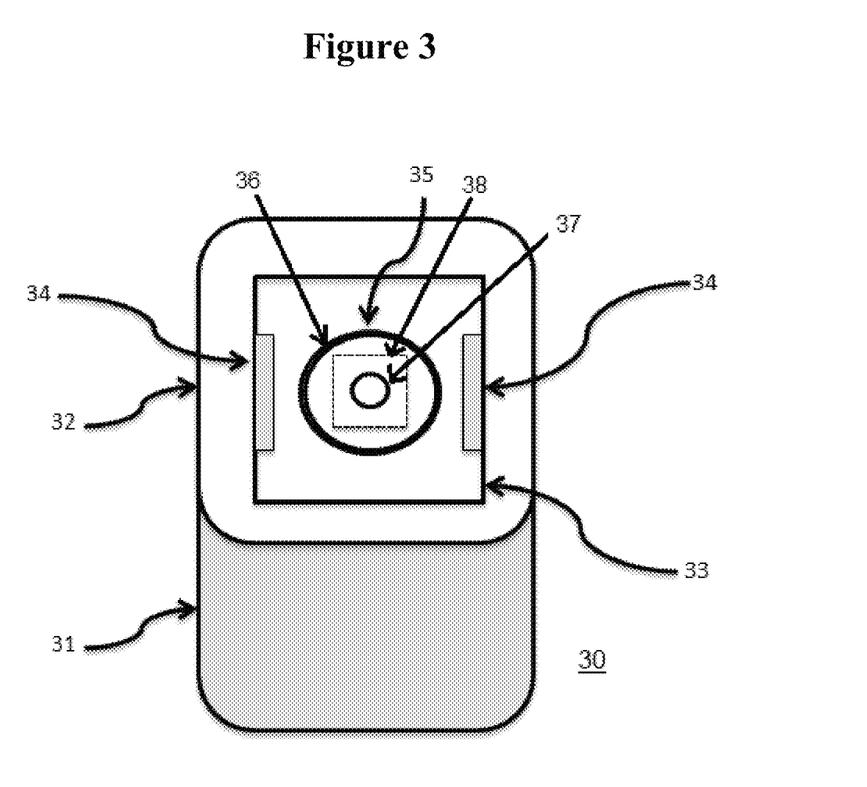
FIG. 3 shows a front view of a clip device in which an example of a lighting device has been secured.

FIG. 3 shows a front view of an embodiment of a lighting device 30 having a back clip portion 31 that will be utilized to affix lighting device 30 to an ideal mounting surface. In some embodiments, back clip portion 31 will reside posterior to a surgical retractor when secured to it. Front clip portion 32 of the lighting device 30 will face towards the surgical field, in the direction of illumination. Located on front clip portion 32 is a lighting element 35 that may have similar components as seen in FIGS. 1A and 1B, including casing 36, LED 37, and circuit board 38. Casing 33 helps secure lighting element 35 to the front portion 32 of the lighting device 30. Locking clasps 34 can be used to secure casing 33 to front portion 32. Casing 33 is preferably plastic and preferably clear or translucent, or in alternative embodiments the casing may have slots or spaces for permitting the light from the LED to pass through.

In preferred embodiments, the light source is an LED or at least two LEDs that are a few millimeters in cross sectional diameter. The LEDs are powered by a battery and have required circuitry to maintain their function. There is a switch or button to turn on the illumination. The light source is attached to a clip that will secure onto a standard operative retractor, or will be imbedded within a disposable suction tip such as a Yankauer suction tip (already in common use) that will be modified in production to house the required LEDs and supporting electronics. The whole construct could be sterilized in a manner similar to other disposable instruments used within the operative theater such as arthroscopic or laparoscopic disposables such as shavers, endo loops, and similar instruments. The circuitry and electronics required for the light source, including the power source and the heat sink, may be modified according to need, so long as the light source remains compact, able to be securely positioned, and sterlizable or disposable.

EXAMPLE 1

A preferred embodiment of the lighting device was investigated. Many deep cavity surgeries require retractors to hold open the operative field to reveal the targeted area. This embodiment of the lighting device uses a circular casing attached to a square clip that can be placed onto a retractor. Using a retractor as an anchor, rather than the patient's tissue, provides more certainty to the way it will be used, including a greater stability and a lower chance of damaging tissue. With few moving parts, the clip is also conceptually simple and sturdier.

The circular casing in this example was slightly greater than the size of a quarter. It housed a lithium-ion battery, three LEDs, and a printed circuit board (PCB). Each LED was about half the size of a pencil eraser and produces natural white light. The device was turned on and off by rotating the casing around the clip. This movement was possible by introducing screw threads to the inside lining of the casing. The entire casing of the prototype and the clip was made by 3D printing.

The main goal of this example was to establish feasibility to create a product solution for surgical lighting. The device must meet four essential feasibility criteria in order to achieve a minimal standard: non-obtrusive, cost-effective, sterilizable, and thermally benign. The device size must be small as to not obstruct to the physician during surgery. The cost of the device must be low to be disposed after a single use to minimize infection risks and eliminate the need for re-sterilization. Finally, the device must withstand the sterilization process and must be thermally benign as to not cause harm to the patient. Other needs that should be considered when designing a new surgical lighting device include: sufficiently illuminant, a fully self-contained system with all components in one unit, ease of setting up and using, versatile for different surgeries, adjustable from a fixed location, and adjustable from the operative field. Thus we can say that there exists a need for a supplemental surgical lighting option that is cost effective, independently portable, and minimally obtrusive, that accurately lights the field, which can be easily adjusted within operative field.

Surgical lighting must provide accurate color so that surgeons have the visual acuity to accurately assess tissue oxygenation. If surgical lighting has too much of a blue hue, the tissue can falsely appear to be hypoxic. Parameters that affect the coloration of the LEDs from the surgical lighting device include the color rending index (CRI), and color correlated temperature (CCT). CRI is a measure of how well the light source renders the color of the object relative to a 3 reference light on a unitless scale of one to 100.7 CCT is a measure of the "warmth" or "coolness" of the light source color appearance. As CCT values decrease, red hues become more visible, i.e. the color temperature becomes "warmer". Conversely, as CCT values increase, blue hues become more visible, i.e. the color temperature becomes "cooler". Guidelines for these parameters are from the Department of Energy (DOE) and the International Electrotechnical Commission (IEC). The values given for CRI and CCT on the specification table are the average values found for the standard overhead lighting shown in Table 1 below.

TABLE 1

| Feature | Value | Unit |
| --- | --- | --- |
| Color rendering index (CRI or $R_a$) | 85-100 | (unitless) |
| Color correlated temperature (CCT) | 2700-6500; neutral standard is approximately 4000 | degrees K |
| Efficacy | no less than 16.7 | lumens/Watt |
| Central illuminance (Ec) | 40,000-160,000; standard is approximately 64,500 | lux (at 1 m from the light emitting surface in the light field center) |
| Beam uniformity characteristic | 0.5 | (unitless) |
| Depth of illumination | no less than 20 | cm |
| Rated useful lifetime (hours of operation at greater than 80 percent of initial light output) | no less than 3 | hours |
| Average cost of device & maintenance | no greater than 200 | USD |
| Maximum tissue temperature (in terms of device heat generation) | 43 | ° C. |

In addition to accurate coloring, the surgical light must meet specific requirements for the characteristics of the light itself including: efficacy, central illuminance (Ec), beam uniformity characteristic, and depth of illumination. Efficacy is the lumens of light produced per watt of input power. Central illuminance is defined as the illuminance at 1 m distance from the light source in the light field center. Beam uniformity characteristic is the ratio of the light field diameters d50 and d10, where the edge of the light field is defined where the illuminance is 50% and 10% Ec, respectively. The greater the value the of the beam uniformity characteristic, the sharper the edge of the lighted field.

Depth of illumination is the distance between the point of maximum illumination intensity and the point of 60% illumination intensity. The values given for efficacy, central illuminance, and beam uniformity on the specification table (Table 1) are the average values found for the standard overhead lighting. Depth of illumination is estimated for an in-body placement lighting device. Guidelines for these parameters are also from the Department of Energy (DOE) and the International Electrotechnical Commission (IEC).

Figure 4:
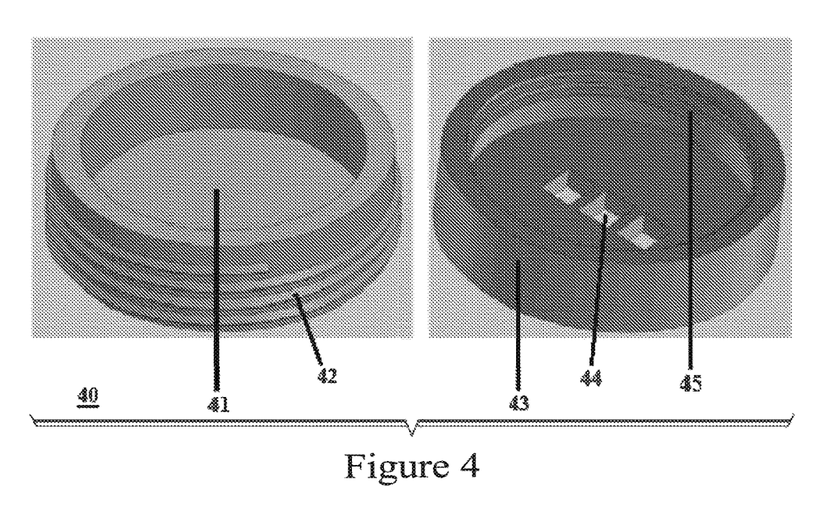
FIG. 4 shows a bottom view of a battery holder of an example of a lighting device and a bottom view of a LED casing in which the battery holder would be screwed into as part of the example lighting device.

Shown in FIG. 4, this example of the lighting device 40 consists of three surface-mounted LEDs (not shown), one lithium-ion coin cell battery (not shown), a circuit board (shown in FIG. 5), an anchoring clip (shown in FIGS. 6A and 6B), and first portion of casing for the battery 41 and a second portion of casing for the LED 43. FIG. 4 shows the CR2032 battery holder casing 41 with a triangular thread profile 42. FIG. 4 also shows a bottom view of the LED casing 43 to which the battery holder would be connected or screwed into, also with a receiving triangular thread profile 45. In this example, LED casing 43 has exterior slots 44 for receiving and mounting the LEDs and for permitting light from the LEDs to exit the device, rather than using a clear or translucent casing. The method of turning on the light is through a screw (twist) mechanism. The on/off capability allows for conservation of battery power and storage of the device in its deactivated state. This screw design was chosen for its simplicity and potential for a low profile. This would facilitate the manufacturing process, keeping the process time short and the cost low. Additionally, the screw mechanism is easy for surgeons to use.

There are a variety of thread profiles, some of which are standardized and others are not. Potential thread profiles include: triangular, semicircular, rectangular, etc. The triangular thread profile was chosen and swept through a helical pattern, because this thread profile was easiest to design and 3D print. When manufacturing a final product, a standard thread profile could also be used. The common thread standards are described by the Unified Thread Standard (used in North America) and the ISO metric screw head (used worldwide). The major difference between these two profiles is the unit of measurement, either in inches or millimeters, respectively. Both profiles were in a trapezoidal shape and were cut at 30° to the vertical. The ACME thread profile is yet another standard that is similar to the two above but is used primarily for threads involved in heavy machinery. The profile is trapezoidal and is the standard because of its ease in manufacturing and utility effectiveness.

The three LEDs that chosen were each rated at 25 lumens. Lumens are a unit of measure of the luminous power emitted from a light source. For reference, high quality bike lights are rated at about 300 lumens, and standard 60 Watt incandescent bulbs are rated at about 800 lumens. Surface-mounted LEDs (SMDs) were used because of their small size and ability to be easily incorporated into a custom-printed design. A single SMD measures only 2.80×3.50× 0.81 mm. Furthermore, SMDs are relatively cheap with a relatively low cost, high lumen-to volume ratio, efficiency, and type of light emitted.

The light emitted from the LEDs must qualify to certain specifications. The LED emits a natural white light with a CCT of 4000 K. As stated previously, reference values for the CCT are around 2700 K-6500 K with the high temperatures related to a blue or "cool" color and the low values related to a yellow or "warm" color. Therefore, a CCT of 4000 K indicates a relatively neutral color appearance. The LED used had a color rendering index (CRI) of 80. While a LED with a higher CRI value might be preferred, the positives of this LED significantly out-weigh this one downside. During the manufacturing process, another LED with a slightly higher price but a better CRI value may be suitable for use.

Figure 5:
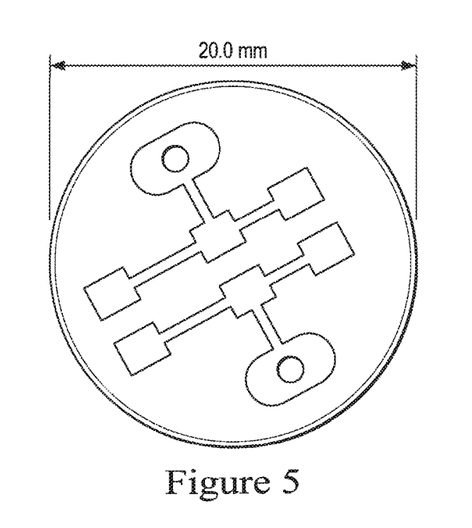
FIG. 5 shows an example circuit board found in an example of a lighting device.

The printed circuit board (PCB) was designed using EAGLE CAD software and is shown in FIG. 5. This PCB was simple, requiring only a voltage-in source, voltage-out source, and parallel wires to each of the three LEDs.

The LED used can be activated in the range of 2.8 to 3.6 V with a 60 mA current, with its peak current at 180 mA. The CR2032 battery was tested on the SMD without a resistor and it was expected that the LED would blow out. However, in an informal experiment in which a single LED was connected directly to the battery, it was found that the setup lasted for more than a week. This prototype does not contain a resistor; as there is resistance already within the LED to draw the current. A resistor may be included in future iterations of the lighting device to lower the risk that the peak current of the LED will be exceeded, blowing out the LED. In the event the resistor value needs to be determined, the following equation can be used:

$$R_{LED} = \frac{V_B - V_{LED}}{I_{LED}}$$

where $V_B$ is the voltage of the battery, and $V_{LED}$ and $I_{LED}$ are the recommended voltage and current respectively. Additional circuit alterations can be added to provide safeguards for in vivo use.

Figures 6A, 6B:
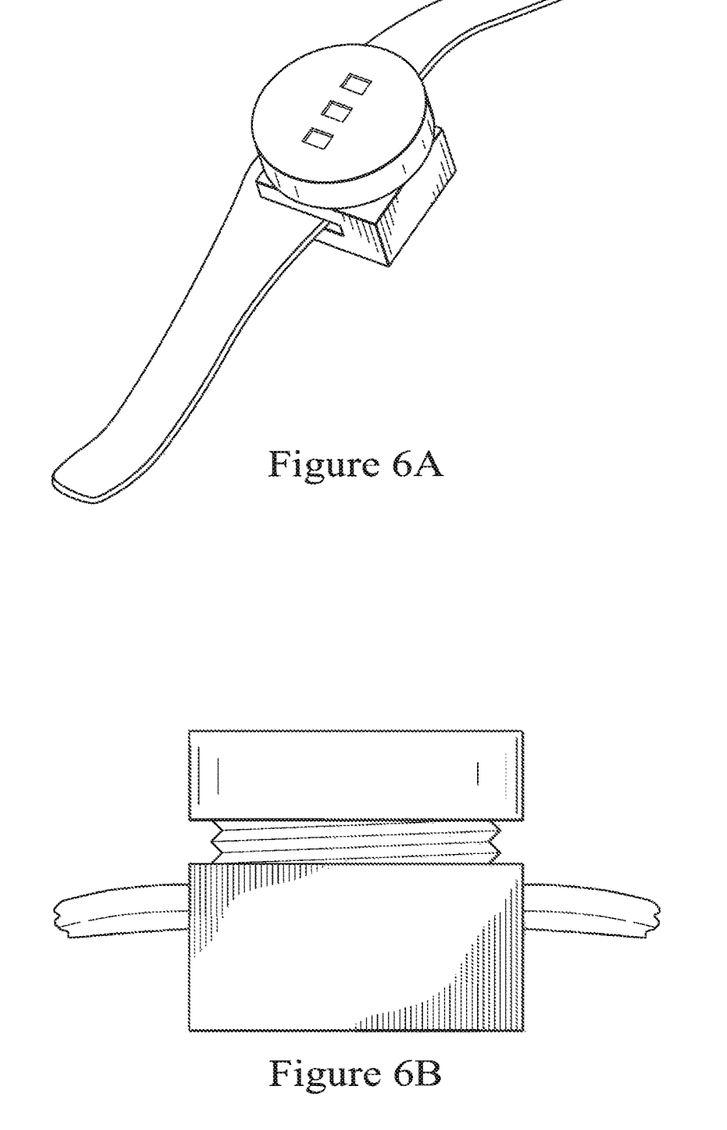

This example uses a static, slide-on clip as the attachment mechanism. The clip had a base with two projections—the parts that actually clamp on to the retractor—on either side (shown in FIG. 6). FIG. 6A shows a top view of the example of the lighting device, with the three LEDs visible through the surface of the casing, attached to or clipped onto a retractor with a clip attached to the bottom of the device. FIG. 6B shows a side view of the example lighting device and attached clip attached to or clipped onto a retractor. The inside face of the clip was lined with a rubber, micro-suction sheet in order to increase resistance between the clip to retractor interface, allowing for the device to stay on. This design was chosen because of simplicity; the clips allow for the light to easily be moved between instruments, as dictated by the particular surgical needs.

A CEN-TECH® digital multimeter was used to measure the power consumption of this circuit. Across each LED was 2.65 volts. The current through one of the LEDs when the three LEDs were placed in parallel was 6.45 mA. Thus, the power consumption for one LED is simply:

$$2.65 \times 0.00645 = 0.017 \text{ Watts}$$

The entire device, with three LEDs, is 3*0.017=0.051 Watts. This is an extremely low value; comparing this to a standard 100 W incandescent bulb which emits 98 W of power as heat. The battery has a capacity of 220 mAh. The following equation will determine how long the LEDs will stay lit:

$$0.220 \text{ Ah} = \frac{0.220 \text{ hr} * C \cdot 3600 \text{ s}}{s \quad 1 \text{ hr}} = 792 \text{ C}.$$

$$792 \text{ C}. \times \frac{s}{3(0.00645)} = 40,930 \text{ seconds} = 11.37 \text{ hrs}$$

Typically, 11.37 hrs is much longer than is needed for standard deep cavity procedures.

Figure 7A:
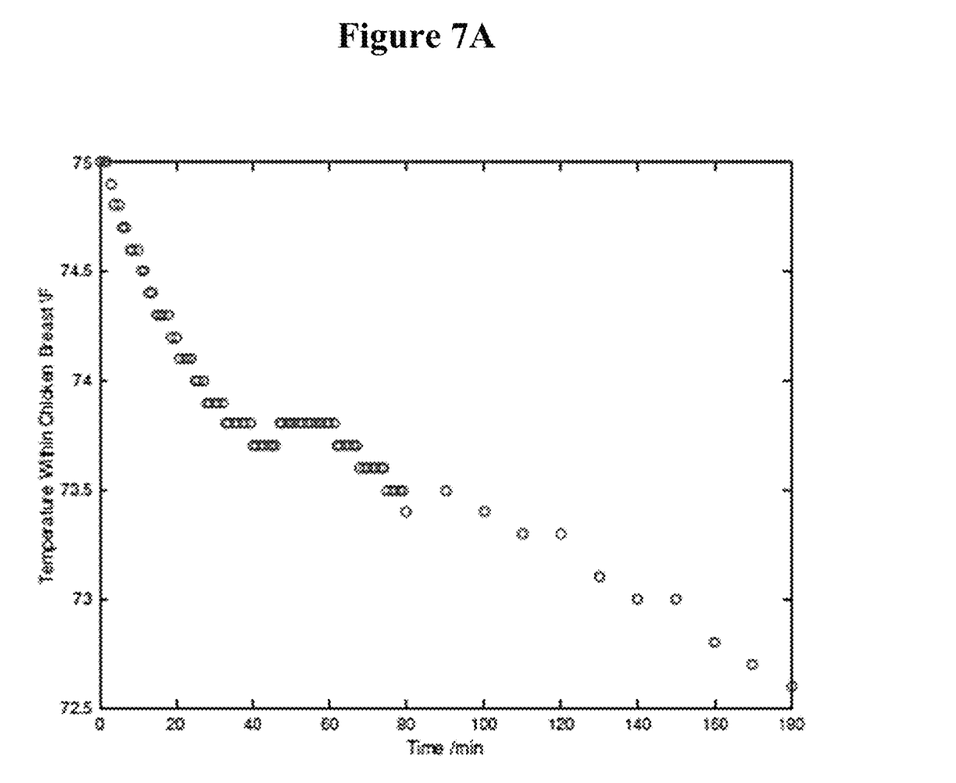
FIG. 7A shows temperature of a chicken breast over time with an example of the lighting device placed 60 mm away from the chicken breast.

In order to reach the thermally benign feasibility criteria, an experiment was conducted to see if the heat generated from the LEDs would result in an increase in tissue temperature. The maximum threshold temperature for tissue is 43° C., or 109.5° F. 0.46 lb of chicken breast was used as a representative of tissue. A digital thermometer probe was inserted into the chicken breast, placing the tip of the probe as close to the surface of the breast as possible. The ambient temperature was set at a constant 74° F. The lighting prototype was placed 60 mm away from the chicken breast for three hours, then again at a 30 mm distance for another three hours. In the first 1.5 hours of the experiment, the temperature was recorded at one minute increments because it was assumed that a greatest change in temperature would be seen in the first part of the experiment. The results from this part are shown in FIG. 7A. Once it was seen that there was an existing trend, the temperature measurements were recorded at 10 minute increments. At the 60 mm distance, there was a total decrease in temperature of 2.5° F. over three hours. At the 30 mm distance, temperature declined slightly over three hours, with the temperature ranging only in a 0.5° F. difference, shown in FIG. 7B.

Figure 7B:
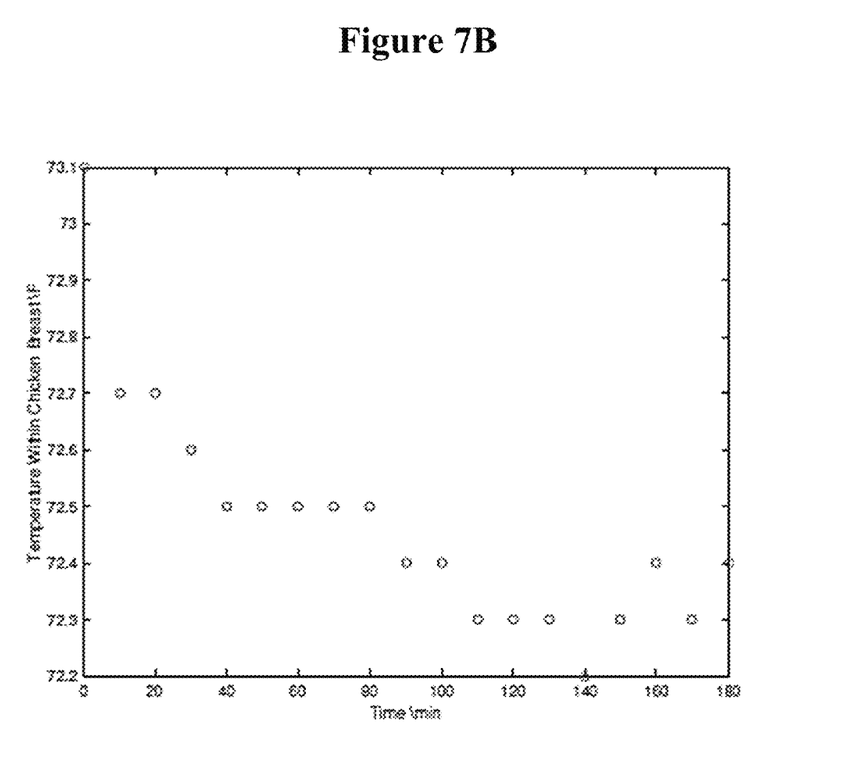
FIG. 7B shows temperature of a chicken breast over time with an example of the lighting device placed 30 mm away from the chicken breast.

The results of these two trials show that external variables such as the temperature of the countertops had much greater influence on the chicken breast than the heat generated from the LEDs. After the experiment, the heat was subjectively tested by directly touching the LEDs after being on for six hours; a significant temperature change was not noted. Thus, the heat generated from the LEDs is negligible, and this prototype is thermally benign.

What is claimed is:

1. A self-contained lighting device, comprising:
   a light source, wherein the light source comprises one or more light-emitting diodes (LEDs), and wherein the LEDs are a few millimeters in cross sectional diameter;
   a power source, wherein said power source is connected to said light source and provides power to said light source;
   a casing, wherein said light source and said power source are connected within said casing and wherein said power source is fully contained within said casing; and
   a mounting means attached to the casing, wherein said mounting means is one or more holes in the casing or a clip attached to the casing,
   wherein the self-contained lighting device is sterilizable and sized for use in a surgical field.

2. The lighting device of claim 1, wherein the light source is contained completely within said casing, wherein said casing is plastic, and wherein the plastic is clear or translucent.

3. The lighting device of claim 1, wherein the casing further comprises one or more exterior slots for receiving the light source, and wherein the light source is positioned within the one or more exterior slots.

4. The lighting device of claim 1, wherein the casing comprises a first portion for containing the power source and a second portion for containing the light source, and wherein the first portion and the second portion are connectable.

* * * * *